(12) United States Patent
Gordon et al.

(10) Patent No.: US 10,197,629 B2
(45) Date of Patent: Feb. 5, 2019

(54) BATTERY RECOMMENDED REPLACEMENT TIME INDICATOR SYSTEM

(71) Applicant: Medtronic, Inc., Minneapolis, MN (US)

(72) Inventors: Charles R. Gordon, Phoenix, AZ (US); James D. Reinke, Maple Grove, MN (US); Val D. Eisele, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 201 days.

(21) Appl. No.: 14/244,913

(22) Filed: Apr. 4, 2014

(65) Prior Publication Data
US 2015/0070022 A1 Mar. 12, 2015

Related U.S. Application Data

(60) Provisional application No. 61/876,182, filed on Sep. 10, 2013.

(51) Int. Cl.
*A61N 1/18* (2006.01)
*G01R 31/36* (2006.01)

(52) U.S. Cl.
CPC .......... *G01R 31/3606* (2013.01); *A61N 1/18* (2013.01); *G01R 31/362* (2013.01)

(58) Field of Classification Search
CPC .............................................. G01R 19/16542
See application file for complete search history.

(56) References Cited

U.S. PATENT DOCUMENTS

| | | | |
|---|---|---|---|
| 4,665,370 A | 5/1987 | Holland | |
| 5,370,668 A * | 12/1994 | Shelton | A61N 1/3708 324/430 |
| 5,391,193 A | 2/1995 | Thompson | |
| 5,438,270 A | 8/1995 | Harper et al. | |
| 5,620,474 A | 4/1997 | Koopman | |
| 5,690,685 A * | 11/1997 | Kroll | A61N 1/378 607/29 |
| 6,108,579 A | 8/2000 | Snell et al. | |
| 6,185,461 B1 | 2/2001 | Er | |

(Continued)

FOREIGN PATENT DOCUMENTS

JP  2007333494  12/2007

OTHER PUBLICATIONS (PCT/US2014/053962) PCT Notification of Transmittal of the International Search Report and the Written Opinion of the International Searching Authority, dated Dec. 1, 2014, 9 pages.

*Primary Examiner* — Robert Grant
*Assistant Examiner* — Tynese McDaniel

(57) ABSTRACT

A method of generating at least one recommended replacement time signal for a battery is provided. The method includes measuring a plurality of associated unloaded and loaded battery voltages. A delta voltage for each associated unloaded and loaded battery voltage is then determined. A select number of delta voltages are averaged. A minimum delta voltage is determined from a plurality of the averaged delta voltages. At least one recommended replacement time signal for the battery is generated with the use of the minimum delta voltage when at least one averaged delta voltage is detected that has at least reached a replacement threshold.

15 Claims, 7 Drawing Sheets

(56) References Cited

U.S. PATENT DOCUMENTS

| | | | |
|---|---|---|---|
| 6,727,708 B1 | 4/2004 | Dougherty et al. | |
| 7,912,546 B2 * | 3/2011 | Eriksson | A61N 1/378 607/29 |
| 8,401,646 B2 | 3/2013 | Stadler et al. | |
| 8,410,783 B2 * | 4/2013 | Staton | G01R 31/3631 320/DIG. 21 |
| 8,415,926 B2 | 4/2013 | Bhardwaj et al. | |
| 8,502,541 B2 * | 8/2013 | Chalfant | G01R 31/362 320/148 |
| 2001/0034541 A1 * | 10/2001 | Lyden | A61N 1/3708 607/29 |
| 2004/0036475 A1 * | 2/2004 | Pascoe | G01R 31/3631 324/425 |
| 2005/0007073 A1 * | 1/2005 | James | G01R 19/16542 320/132 |
| 2008/0306569 A1 * | 12/2008 | Tobacman | A61N 1/3708 607/29 |
| 2009/0273349 A1 * | 11/2009 | Rondoni | A61N 1/3708 324/430 |
| 2011/0074434 A1 | 3/2011 | Staton | |
| 2011/0178743 A1 * | 7/2011 | Krause | H01M 8/04671 702/63 |
| 2012/0105071 A1 | 5/2012 | Chalfant et al. | |
| 2012/0276445 A1 * | 11/2012 | Xu | H01M 2/1653 429/199 |
| 2013/0049762 A1 * | 2/2013 | Ogg | H01M 10/4207 324/433 |
| 2014/0167706 A1 * | 6/2014 | Sun | H02J 7/0081 320/160 |

* cited by examiner

BATTERY RECOMMENDED REPLACEMENT TIME INDICATOR SYSTEM

BACKGROUND

Implantable medical devices such as cardioverter/defibrillators are commonly configured to treat cardiac arrhythmias by delivering high voltage energy pulses to cardiac tissue. Implantable defibrillators commonly deliver therapy by way of electrodes positioned within or near the heart of the patient. Such therapy includes defibrillation therapy, which utilizes a sudden, high energy pulse designed to shock the heart of the patient out of a cardiac arrhythmia if and when a cardiac arrhythmia occurs. Implantable defibrillators also commonly incorporate pacing therapy, which utilizes very low energy pulses designed to trigger cardiac contractions in lieu of an adequately frequent natural heart beat of the patient.

Implantable defibrillators commonly incorporate a power source, such as a battery, which provides operational power to the componentry of the defibrillator, including electronics which manage the function of the device, monitor the condition of the patient in which the device is implanted and deliver therapy to the patient. Many or most device functions operate effectively continually, such as sensing the cardiac condition of the patient, or frequently, such as cardiac pacing therapy delivery in certain patients, and thus account for steady, predictable and, usually, low-level drains on the battery capacity. Defibrillation therapy, by contrast, usually occurs very infrequently in most patients, commonly with months or years between defibrillation therapy deliveries, owing to the generally infrequent occurrence of arrhythmias which require treatment. As such, defibrillation therapy is, from a standpoint of battery management, a large, sudden, essentially random drain on the battery of the implantable defibrillator.

Because implantable defibrillators often provide life-sustaining therapy to the patients, it is essential to the well-being of the patient to understand how long the battery may be expected to last until the battery will be discharged to a point of being unable to provide reliable therapy. Hence, with an implantable medical device (IMD), it is necessary to provide an indication prior to battery depletion to enable the device to be replaced prior to loss of function of the IMD. This is commonly referred to as an elective replacement indicator (ERI) or a recommended replacement time (RRT). One method used to set an RRT threshold is with the use of a time based algorithm that is started at the time of the implant of the IMD. This time based algorithm type of RRT system is adequate when the battery used in the IMD has a relatively large capacity and its performance is predictable. However, as IMDs shrink in size, the batteries used in the IMDs also need to shrink in size. Smaller batteries tend to have reduced capacity. Moreover, the performance of these smaller size batteries can vary broadly in both voltage performance and impedance performance. Because of these characteristics, the use of a time based algorithm may be unreliable for a smaller battery.

For the reasons stated above and for other reasons stated below which will become apparent to those skilled in the art upon reading and understanding the present specification, there is a need in the art for an effective and efficient method and system to determine an RRT of a battery.

SUMMARY OF INVENTION

The above-mentioned problems of current systems are addressed by embodiments of the present invention and will be understood by reading and studying the following specification. The following summary is made by way of example and not by way of limitation. It is merely provided to aid the reader in understanding some of the aspects of the invention.

In an embodiment, a method to determine a threshold point of a battery is provided. The method includes measuring a plurality of associated loaded and unloaded battery voltages; determining a delta voltage for each associated loaded and unloaded battery voltages; determining a minimum delta voltage from a plurality of delta voltages; and using the minimum delta voltage in generating a threshold signal.

In an another embodiment, a method of generating at least one recommended replacement time signal for a battery is provided. The method includes measuring a plurality of associated unloaded and loaded battery voltages; determining a delta voltage for each associated unloaded and loaded battery voltages; averaging a select number of delta voltages; determining a minimum delta voltage from a plurality of averaged delta voltages; generating the at least one recommended replacement time signal for the battery with the use of the minimum delta voltage when at least one averaged delta voltage is detected that has at least reached a replacement threshold.

In an embodiment, a battery recommended replacement time system is provided. The system includes a battery monitor, a circuit, a signal generator, a memory and a controller. The battery monitor is coupled to measure a voltage of a battery. The circuit is selectively coupled to the battery to provide a current load to the battery. The signal generator is configured to generate a recommended replacement time threshold signal. The memory is used to store instructions and data. The memory includes instructions to determine a minimum delta voltage from a plurality of averaged delta voltages. The controller is in communication with the memory, the battery monitor and the signal generator. The controller is configured to selectively couple the circuit to the battery. The controller is also configured to execute the instruction to determine the minimum delta voltage from the plurality of averaged voltages. The controller still further is configured to implement the instructions and process data relating to the determined minimum delta voltage to activate the signal generator when a delta voltage is detected by the battery monitor that has reached a determined replacement threshold.

In an embodiment, a multitude of thresholds are set after the minimum delta voltage is determined. The controller in this embodiment is configured to use the multitude of thresholds to set up a gas gauge like configuration to monitor the depletion of the battery.

In an embodiment, the controller is configured to control the timing of the measurement of associated delta voltages to at least two of before, during and after a current pulse.

In an embodiment, the controller is configured to average a plurality of delta voltages to reduce false measurements due to spikes when measuring the unloaded and loaded voltages.

In an embodiment, the controller is configured wait a specified time after implantation of the battery before collecting data to reduce the possibilities of generating a false RRT because of early artifacts (spikes) caused by the initial activation and warming up period of the battery.

In an embodiment, the controller is configured to recognize trends in collected delta voltage averages and make determinations based on the trends.

In an embodiment, the controller is configure to determine a minimum delta voltage average based on a recognized trend in measured delta voltages.

In an embodiment, the controller is configured to generally determine a midpoint of the life of the battery based on a recognized trend in the delta voltage averages.

BRIEF DESCRIPTION OF THE DRAWINGS

The present invention can be more easily understood and further advantages and uses thereof will be more readily apparent, when considered in view of the detailed description and the following figures in which.

In accordance with common practice, the various described features are not drawn to scale but are drawn to emphasize specific features relevant to the present invention. Reference characters denote like elements throughout Figures and text.

DETAILED DESCRIPTION

In the following detailed description, reference is made to the accompanying drawings, which form a part hereof, and in which is shown by way of illustration specific embodiments in which the inventions may be practiced. These embodiments are described in sufficient detail to enable those skilled in the art to practice the invention, and it is to be understood that other embodiments may be utilized and that changes may be made without departing from the spirit and scope of the present invention. The following detailed description is, therefore, not to be taken in a limiting sense, and the scope of the present invention is defined only by the claims and equivalents thereof.

Embodiments of the present invention provide a dynamic battery monitoring system that provides a reliable RRT. Embodiments of the present invention monitor the battery for a delta voltage that is used to determine the RRT. In particular, a delta voltage is determined by comparing a voltage of the battery when it is unloaded to the voltage of the battery when it is loaded. The delta voltage is tracked over a period of time to determine a minimum delta voltage. The minimum delta voltage is then used to set a threshold. When at least one delta voltage is measured at or above the threshold, a RRT signal is generated to indicate the state of the battery. Although embodiments are described below as being used with an IMD, the system has an application to any type of device where you need to know the RRT of the device's battery. It is especially useful with batteries where there is a sharp drop off in discharge at the end of the life of the battery as discussed further below.

Figure 1:
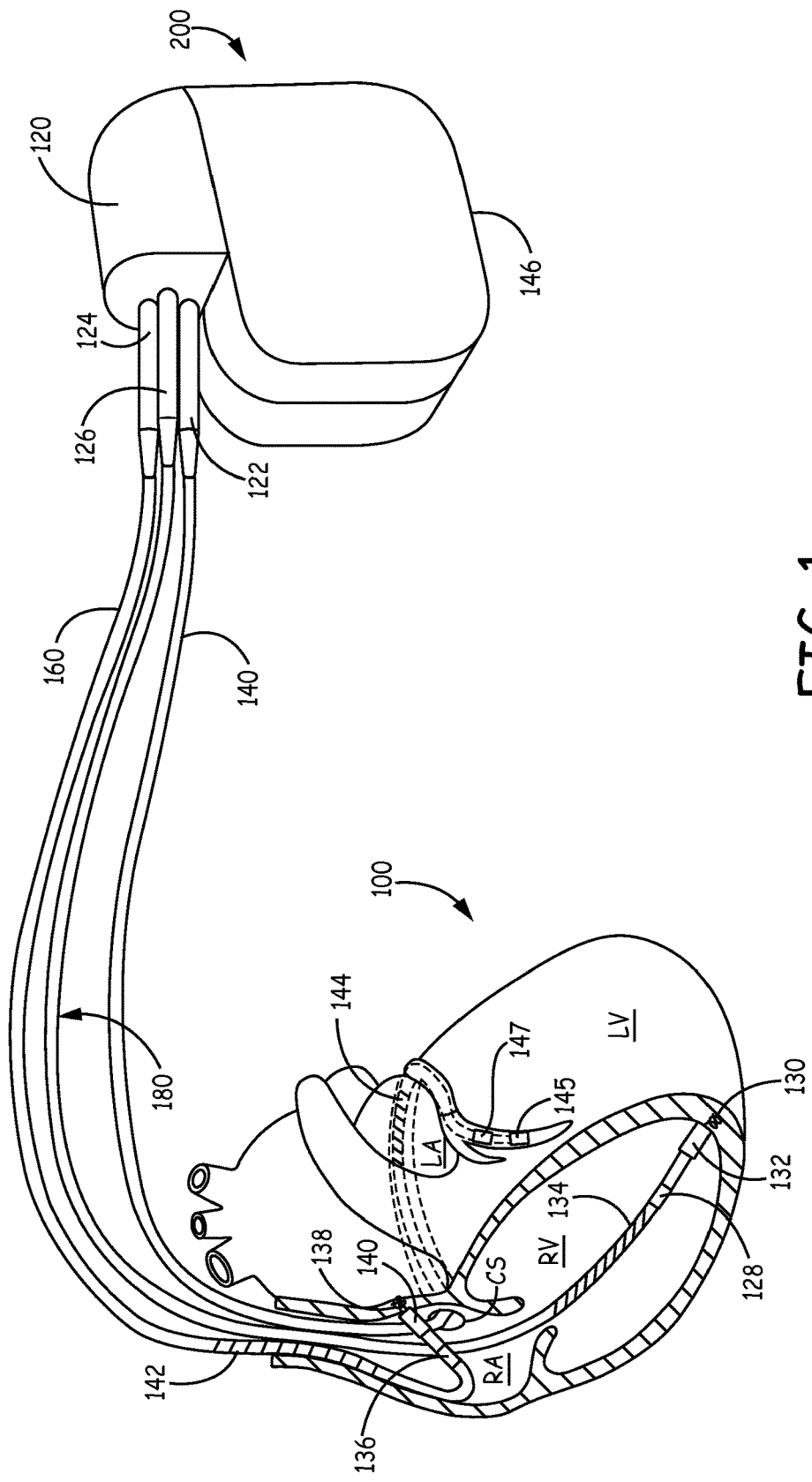
FIG. 1 is a conceptual diagram illustrating the implementation of an IMD of an embodiment of the present invention.

An example of an IMD that may implement the battery monitor system is provided in FIG. 1. In FIG. 1 the IMD 200 is a cardiac defibrillator with a pacing function. The pacing function may treat bradycardia and may resynchronize heart 100 in conditions of patient heart failure. Such a defibrillator is known as a cardiac resynchronization therapy defibrillator, known in the art as a CRT-D device. Other example IMDs 200 include a cardioverter/defibrillator without a pacing function or with a pacing function but without a cardiac resynchronization feature. In addition, as discussed above, the implantable medical device 200 may be any device which incorporates pulse draws from a battery. The implantable medical device 200 example of FIG. 1 is coupled to heart 100 by way of coronary sinus lead 140, right atrial lead 160, and right ventricular lead 180. IMD 200 includes a connector block 120 that receives connectors 122, 124 and 126 positioned on the proximal ends of the respective coronary sinus lead 140, right atrial lead 160 and right ventricular lead 180. Connectors 122, 124 and 126 provide electrical connectivity between leads 140, 160, 180 and electronic circuitry (shown in FIG. 2) within implantable medical device 200.

In this example, a ring electrode 128, extendable helix electrode 130 mounted retractably within an electrode head 132, and coil electrode 134 are positioned on right ventricular lead 180. The ring electrode 128, the extendable helix electrode 130 and the coil electrode 134 are electrically coupled to an insulated conductor within right ventricular lead 180. As illustrated, right ventricular lead 180 is positioned such that its distal end is in the right ventricle for sensing right ventricular cardiac signals and delivering pacing or shocking pulses in the right ventricle. The proximal end of the insulated conductors are coupled to corresponding connectors carried by bifurcated connector 126 for providing electrical connection to implantable medical device 200.

Right atrial lead 160 in this example, includes a ring electrode 136 and extendable helix electrode 138, mounted retractably within electrode head 140, for sensing and pacing in the right atrium. Right atrial lead 160, in this example, includes coil electrode 142 to deliver high-energy shock therapy. Right atrial lead 160 is positioned such that its distal end is in the vicinity of the right atrium and the superior vena cava. Ring electrode 136, helix electrode 138 and coil electrode 142, in this example, are connected to an insulated conductor within the body of right atrial lead 160. The insulated conductor is coupled at its proximal end to bifurcated connector 124 as shown.

Coronary sinus lead 140, in this example, includes defibrillation coil electrode 144 that may be used in combination with coil electrode 134 or coil electrode 142 for delivering electrical shocks for cardioversion and defibrillation therapies. Coronary sinus lead 140 may be advanced within the vasculature of the left side of heart 100 via the coronary sinus and great cardiac vein. In various embodiments, coronary sinus lead 140 may also include a distal tip electrode 145 and ring electrode 147 for pacing and sensing functions in the left chambers of the heart. Coil electrode 144 is coupled to an insulated conductor within the body of lead 140. The insulated conductor is coupled at its proximal end to connector 122.

Electrodes 128, 130, 136 and 138 may be used to form bipolar pairs. Various ones of such bipolar pairs may be referred to as "tip-to-ring" pairs. Electrodes 128, 130, 136 and 138 may likewise be utilized individually in unipolar configuration with implantable medical device housing 146 serving as an indifferent electrode, commonly referred to as the "can" or "case" electrode. Housing 146 may also serve as a subcutaneous defibrillation electrode in combination with one or more of coil electrodes 134, 142 and 144 for defibrillation of atria or ventricles of heart 100. In various embodiments, alternate lead systems may be substituted for the lead system of the example embodiment of FIG. 1. Moreover, leads for use with a single chamber, dual chamber, or multichamber implantable medical devices may be utilized. The IMD 200 delivers pacing pulses via any bipolar or unipolar combination of electrodes 128, 130, 134,144, 136, 138, 142, 144, 145 and 147. The IMD may also deliver cardioversion or defibrillation pulses to the heart 100 via combination of electrodes 128, 130, 134, 136, 138, 142, 144, 145 and 147.

Figure 2:
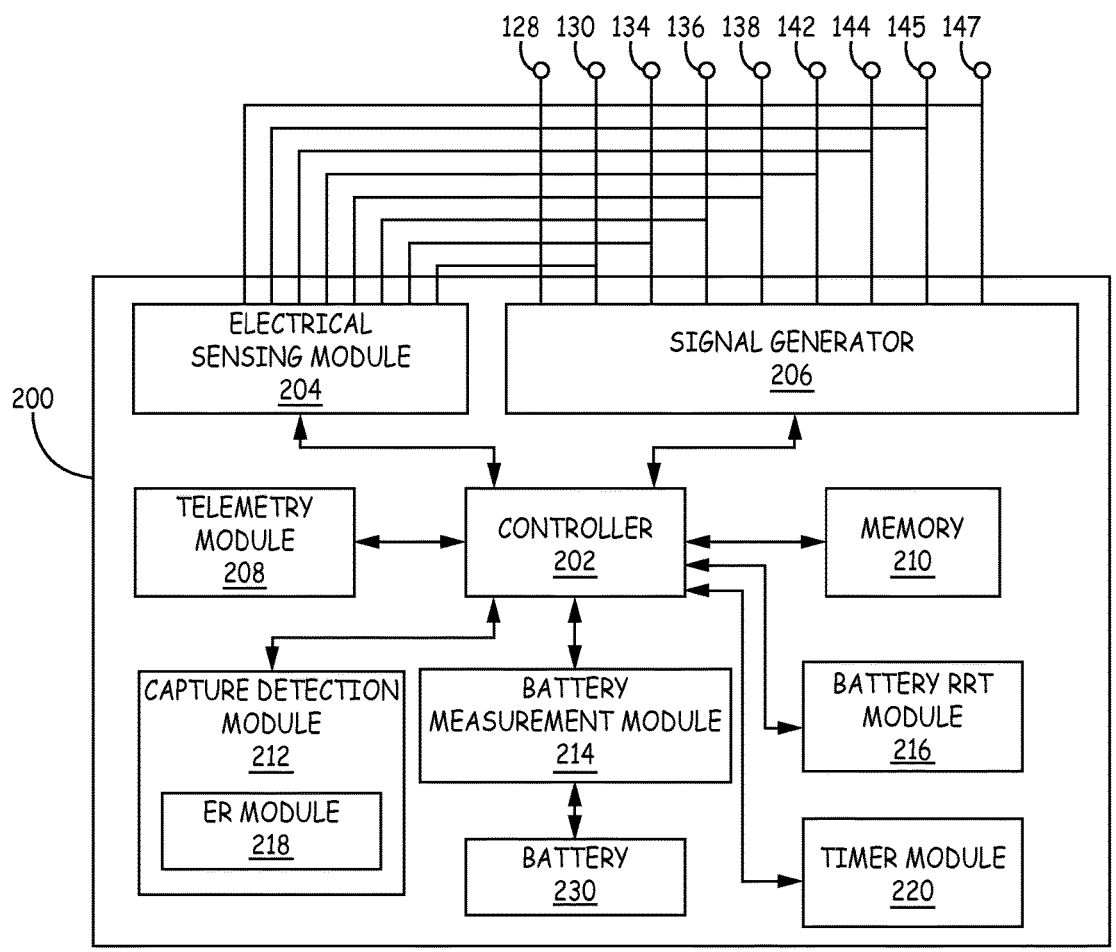
FIG. 2 is a block diagram of the IMD of FIG. 1.

Referring to FIG. 2, a block diagram illustrating an example configuration of IMD 200 of an embodiment is illustrated. In the example illustrated in FIG. 2, IMD 200 includes a controller 202, a memory 210, a signal generator 206, an electrical sensing module 204, a telemetry module 208, a capture detection module 212, a battery measurement module 214, a battery RRT module 216, a timer module 220, a battery 230. Further in this example, the capture detection module 212 includes an evoked response detection module 218.

The controller 202 (processor) may include any one or more of a microprocessor, a digital signal processor (DSP), application specific integrated circuit (ASIC), a field program gate array (FPGA), or equivalent discrete or integrated logic circuitry. In some example embodiments, controller 202 may include multiple components, such as any combination of one or more microprocessors, one or more controllers, one or more DSPs, one or more ASICs, one or more FPGAs, as well as other discrete or integrated logic circuitry. The functions attributed to controller 202 herein may be embodied as software, firmware, hardware or any combination thereof. Memory 210 may include computer-readable instructions that, when executed by controller 202 provide functions of the IMD 200. Such functions include the functions of the capture detection module 212, the battery measurement module 214, the signal generator 206, the telemetry module 208 and the battery RRT module 216. The computer readable instructions may be encoded within the memory 210. Memory 210 may comprise computer readable storage media including any volatile, nonvolatile, magnetic, optical, or electrical media, such as, but not limited to, a random access memory (RAM), read-only memory (ROM), nonvolatile RAM (NVRAM), electrically-erasable programmable ROM (EEPROM), flash memory, or any other storage media.

As discussed above, controller 202 controls signal generator 206 to deliver stimulation therapy, e.g., cardiac pacing or cardiac resynchronization therapy (CRT), to heart 100 according to a selected one or more therapy programs, which may be stored in memory 210. Signal generator 206 is electrically coupled to electrodes 128, 130, 134, 136, 138, 142, 144, 145 and 147 via conductors of the respective leads 140, 160, and 180. The signal generator 206 may include a switch module (not shown) to select via data/address bus, which of the available electrodes 128, 130, 134, 136, 138, 142, 144, 145 and 147 are used to deliver pulses, such as pacing pulses and stimulus pulses. The electrical sensing module 204 monitors signals from at least one of electrodes 128, 130, 134, 136, 138, 142, 144, 145 and 147 in order to monitor electrical activity of the heart 100. The electrical sensing module 204 may also include a switch module (not shown) to select which of the available electrodes 128, 130, 134, 136, 138, 142, 144, 145 and 147 are used to sense the cardiac activity.

Memory 210 stores intervals, counters, or other data used by the controller 202 to control the delivery of pacing pulses by signal generator 206. Such data may include, but is not limited to, intervals and counters used by processor 202 to control the delivery of pacing pulses to one or both of the left and right ventricles for CRT. The intervals and/or counters are, in some examples, used by controller 202 to control the timing and delivery of pacing pulses relative to an intrinsic or paced event, e.g., in another chamber. One of the functions of the capture detection module 212, is detecting capture and loss of capture (LOC) during capture detection tests. Capture detection module 212 uses timer module 220 to determine when to deliver pacing pulses and to determine conduction times between chambers of the heart. The capture detection module 212 uses the evoke response detection module 218 for detecting the amplitude and timing of an evoked response which may be used additionally or alternatively for detecting capture or LOC.

Battery 230 provides power to operate each of the electrical components of the IMD 200. The components may include the controller 202, the memory 210, the signal generator 206, the electrical sensing module 204, the telemetry module 208, the timer module 220 and the capture detection module 212. As discussed above, with IMDs it is necessary to provide an indication that the battery should be replaced prior to battery depletion and the loss of function of the IMD. This indication is, referred to as the RRT. Batteries made of different chemistry exhibit different voltage and impedance characteristics as the battery is discharged over its life. Furthermore, different cells manufactured with the same chemistry in the same design, exhibit slightly different voltage and impedance characteristics over the life of the battery. That is, the chemistry of each battery creates a unique situation for prediction of remaining longevity. It is desired to maximize the longevity of each device based upon its unique characteristics rather than using single criteria for all devices. Other types of IMDs that may implement this battery technology are implantable hemodynamic monitor, implantable loop recorders and, as discussed above, any other device in which it is beneficial to have an RRT.

Figure 3:
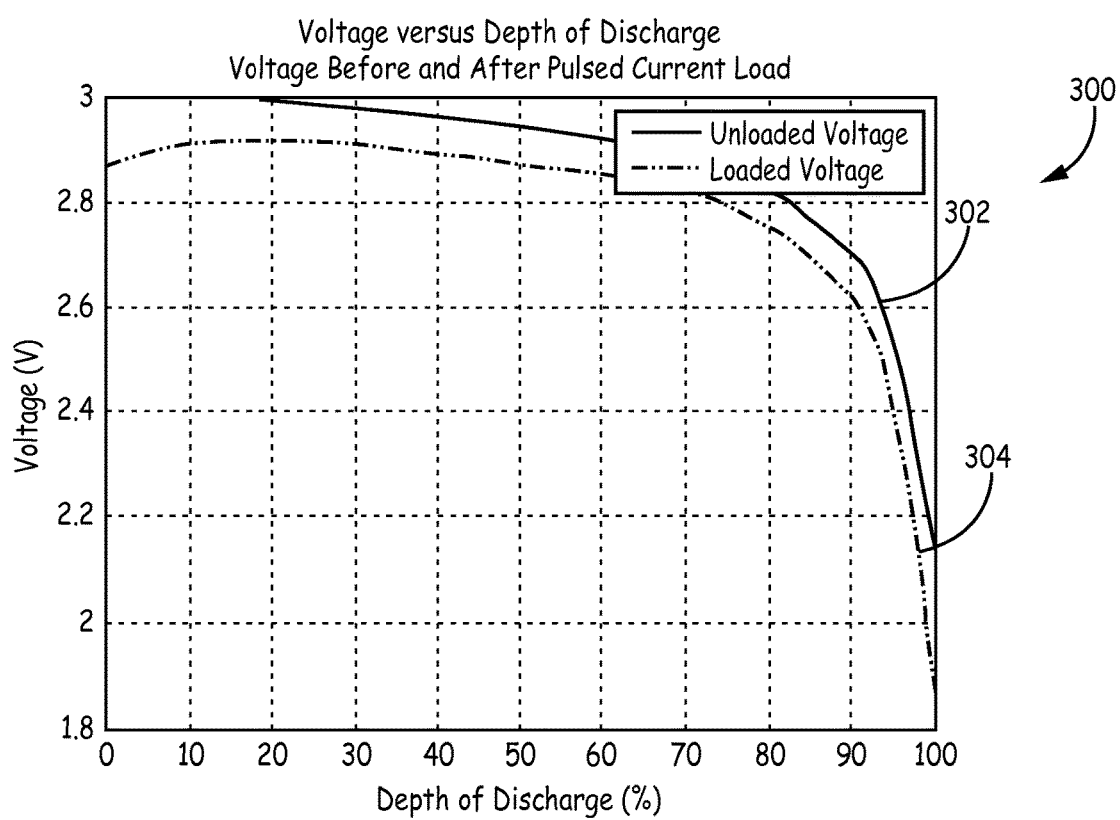
FIG. 3 is an unloaded/loaded voltage over depth of discharge graph of a battery.
Figure 4:
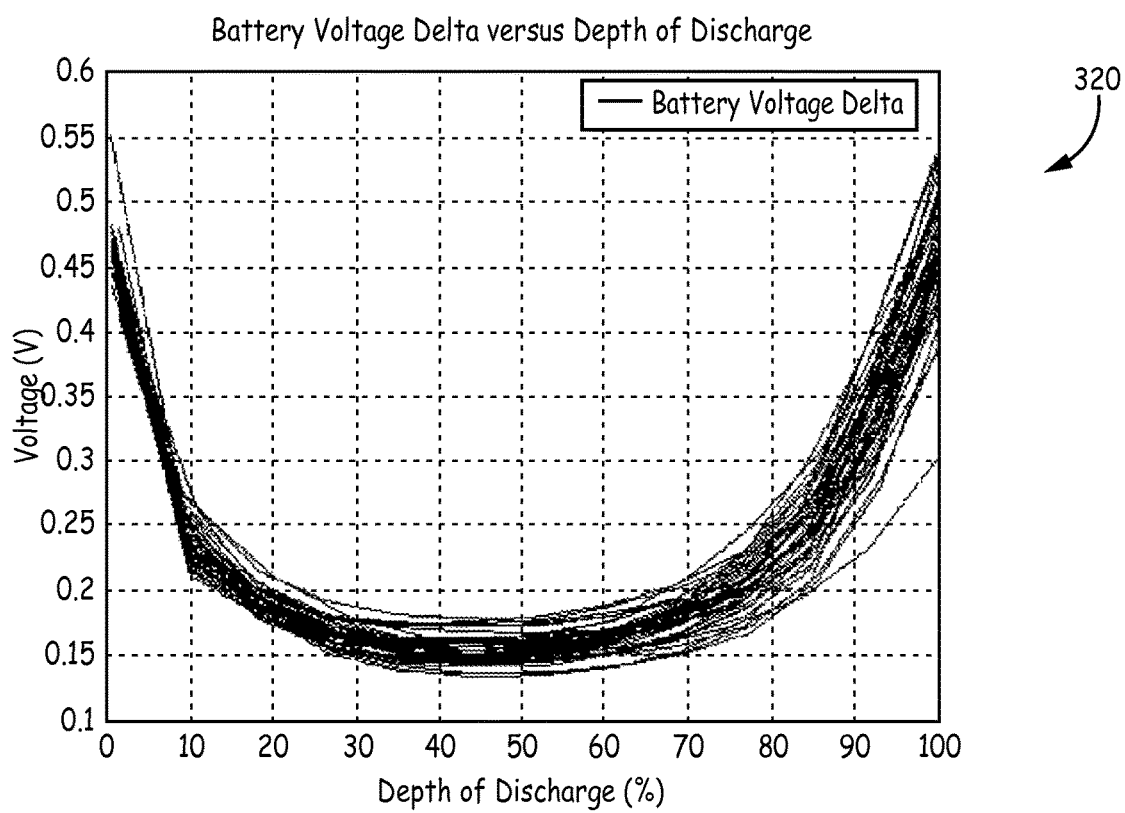
FIG. 4 is a delta voltage of a set of batteries over depth of charge graph of the battery.

Embodiments of the present disclosure provide an RRT indicator that is effective with battery chemistry which has an abrupt increase in impedance and drop off in voltage at the end of the battery life. An example of such a battery is a lithium carbon mono fluoride battery (Li—CFx). A Li—CFx battery provides a relatively small foot print. Also, a Li—CFx battery is highly reliability and has a relatively high capacity. In addition, this type of battery has a relatively low output impedance over its useful life. However, one drawback to a Li—CFx battery is that the voltage decreases and the impedance rises quickly near the end of the battery's life. This makes it difficult to provide sufficient warning of the battery depletion for all cells. FIG. 3 illustrates an unloaded/loaded voltage to depth of discharge graph 300 for a typical unloaded and loaded (500 uA) battery voltage measurement 302 and 304 for a Li—Cfx cell as a function of depth of depletion. As illustrated, the voltage drops sharply towards the end of the discharge. In an embodiment, the battery RRT module 216 includes a circuit to selectively apply a current load to the battery to obtain the loaded voltage battery readings. In other embodiments, other functions of the IMD are used to supply the current load. FIG. 4 illustrates a delta voltage versus depth of charge graph 320. The voltage delta versus depth of charge graph 320 shows how the delta voltage between loaded and unloaded battery voltage measurements varies as a function of depth depletion for a number of cells. As can be seen from the plot, different individual cells have different characteristics with some providing more or less capacity and some providing lower or higher delta voltage under load.

In embodiments, an RRT algorithm is used that defines a threshold for RRT that is based on a relative impedance measurement rather than absolute impedance. The advantage of this is that the accuracy of the load current is not particularly important therein enabling either the dedicated current source load to be used or a high current circuit as a source of the load current. It also allows for greater accuracy even with large variability in impedance from cell to cell. The algorithm is based on the difference in battery voltage measurements taken before the current load is applied and while the battery load is applied. Embodiments of the algorithm include filtering to make the RRT prediction less dependent on errors or noise in a single measurement. Furthermore, in an embodiment, the algorithm prevents premature indication of RRT by waiting until approximately 20% of expected device life has lapsed.

Figure 5:
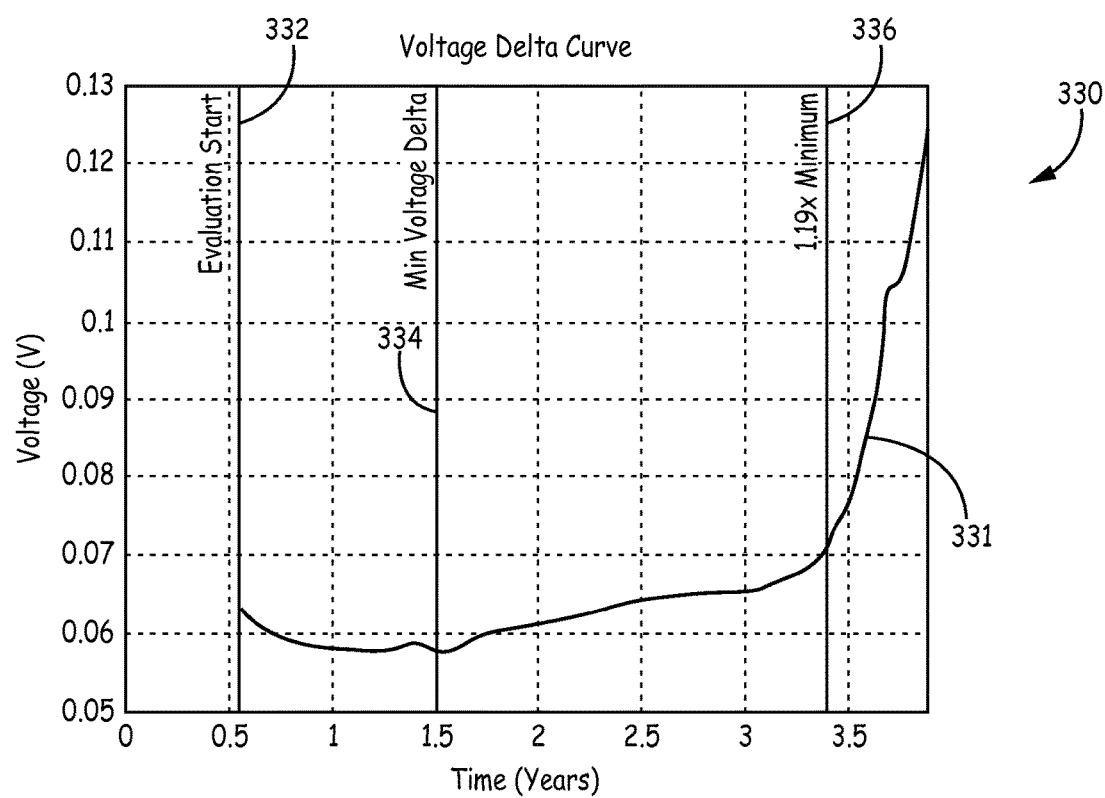
FIG. 5 is a delta voltage curve over time graph for the battery.

Referring to FIG. 5, a delta voltage curve over time graph 330 that graphically represents how an embodiment of the algorithm works. Graph 330 shows the average delta voltage 331 between loaded and unloaded battery voltage measurements over time. The data 331 represents a moving average of approximately 16 days of data. As can be seen from the graph, the delta voltage is higher at both the beginning and the end of the battery life. Moreover, the delta voltage 331 reaches a minimum near the middle of the battery life. The vertical evaluation start line 332, which is approximately 20% of the way across the graph, shows when RRT checking is enabled. The minimum voltage delta vertical line 334 indicates where the minimum delta voltage occurs. The algorithm scores the minimum value and calculates a threshold to be used for the RRT indication based on percentage above the minimum value. In this example, the percentage is 19% larger than the minimum. Also shown on graph 330 is 1.19× minimum trigger vertical line 336 which is the predetermined RRT threshold used to indicate when a signal is to be generated regarding the status of the battery 230. 19% is determined by experimentation and modeling of the characteristics of the battery to be used. Hence, different battery chemistry will have a different minimal trigger. Moreover, as discussed further below, embodiments may have more than one trigger value. Further discussion on the determination of the percentage is provided below.

In embodiments, a dynamic system is used that establishes at least one threshold for what is good and bad based on individual cell characteristics of the battery 230 over time. By trending the delta voltage over time and finding the minimum delta voltage and then looking for a substantial increase in the delta voltage versus the minimum delta voltage, an accurate precursor to the end of the useful battery life can be predicted. One benefit to this system is that since the algorithm used implements a purely ratiometric determination, the need of an accurate current load is diminished. The current load just needs to be large enough to get a reasonably accurate measurement of the delta voltage.

Figure 6:
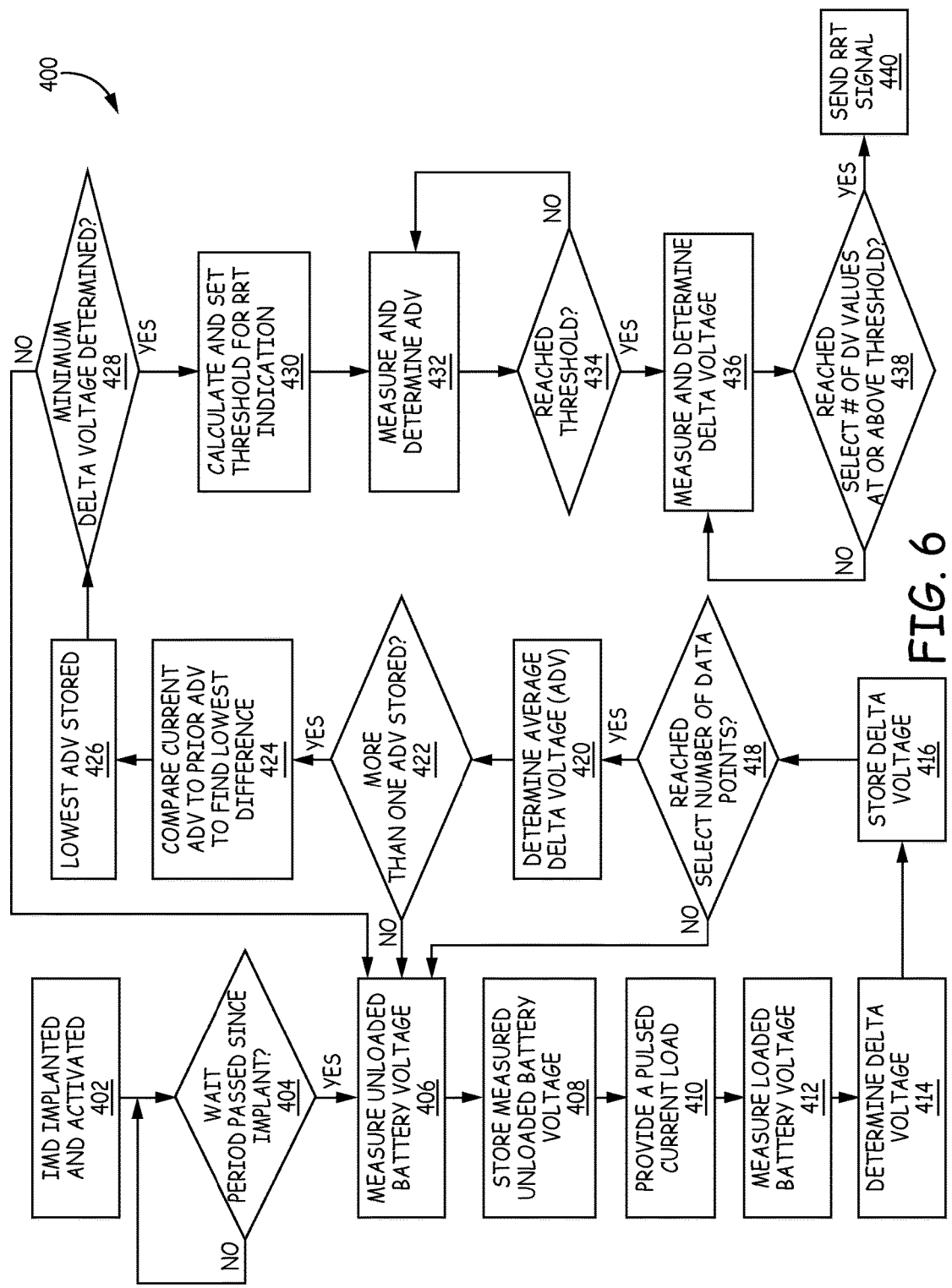
FIG. 6 is a RRT flow diagram of one embodiment of the present invention.

FIG. 6 is a RRT flow diagram 400 of an example embodiment. The process starts by implanting and activating the IMD 200 (402). In one embodiment, the controller 202 then monitors if a select amount of time after implant of the IMD 200 has passed (404). Waiting the select amount of time (wait period) before starting to gather data eliminates the possibilities of generating a false RRT because early artifacts (spikes) caused by the initial activation and warming up period of the battery. An example wait period is 30 days, although different wait periods before activation can be used depending on the characteristics of the battery used. Moreover, in some embodiments, trend data is gathered at implant to generate battery data. After the wait period has passed (404), data used to determine the RRT is started to be collected. In particular, this process starts by measuring the voltage of the battery when it is unloaded (406). This is done with the battery measurement module 214. The measurement is then stored in memory 210 (408). The process continues by providing a pulsed current load (410). The pulsed current load can come from one of the functions of the IMD 200 such as, but not limited to, a transmitter in the telemetry module 208. Otherwise the pulsed current load can be generated with components of the IMD 200 that are specifically designed for the battery load measurement such as circuitry in the battery RRT module 216 that is selectively coupled to the battery 230 by the controller 202. An example current load used is 500 uA, although any current load can be used as long as it is large enough to produce a measurable delta voltage and is small enough that it does not cause the battery voltage to drop so low that the circuitry malfunctions. While the current load is being applied, the battery voltage is measured (412). A delta voltage, which is the difference between the stored unloaded voltage and the load voltage, is then determined (414). The delta voltage is stored in memory 210. In the embodiment of FIG. 6, an average of delta voltages is used to reduce false measurements due to spikes when measuring the unloaded and load voltages. In this embodiment, the controller 202 collects delta voltage data points and stores them until a select number of data points (delta voltage readings) are reached (418). In an embodiment, the delta voltage is collected once a day for 16 days and then averaged. However, the number of data collections per day and the number of days collected can vary. Once the select number of data points are collected at (418), an average delta voltage is determined and stored (420). In an embodiment, it is then determined if there is more than one average delta voltage stored (422). If there is not, the process continues collecting data at (406). If there is more than one stored average voltage (422), the minimum voltage between them is determined (424). The lowest averaged delta voltage is stored (426).

The minimum delta voltage is then determined (428). In one embodiment this is done by trending the collected average delta voltage. That is, in this embodiment, if the delta voltage data points are trending upward, it is likely you had previously reached the minimum. This is illustrated in the table in FIG. 5. Hence, once the upward trend is encountered, the lowest average delta voltage you have stored will be set as the minimum delta voltage. If the upward trend is not encountered in this embodiment, the process continues at (406). In another embodiment, a set time can be used. When the time expires, the lowest average delta voltage stored is the minimum voltage. Once the minimal delta voltage has been determined, a threshold for the RRT indication is calculated (430). In an embodiment the threshold is a select percentage above the minimum delta voltage. For example, with the Li—Cfx type battery, the percentage above the minimum delta voltage is around 19%. In this example then, the threshold value is 1.19 times the minimum delta voltage. As discussed above, the percentage above the minimum delta voltage is predetermined by experimentation and modeling of the battery's characteristics. For example, the percentage can be determined by comparing the performance of a nominal test battery with a three sigma test battery (worst performance battery) and applying measured data regarding their performance to a numerical computation algorithm created in program such a MATLAB®. The modeling is used to determine an optimum threshold trigger in both batteries that maximizes useful the life of the three sigma battery while minimizes the shortening of the life of the nominal battery. From this model the percentage is determined. As discussed above, other batteries would have different percentages depending on the batteries characteristics. For example, the Li—Cfx may have a nominal impedance and its percentage value is around 19%. A battery with a relatively high impedance may result in the use of a percentage around 25% and a battery with a relatively low impedance may result in the use of percentage around 15%. As stated above, the percentage above the minimum delta voltage is determined by experimentation and modeling of the characteristics of the battery being used.

Once the threshold is determined, delta voltage data is gathered (432) similar to steps (406) through (418). The number of data points for each averaged set may be lessened as the delta voltage approaches the threshold. Once a delta voltage average is determined at (432), it is determined if that average has reached or is above the threshold (434). In one embodiment, a low battery ratio (LBR) equation is used to determine if the threshold is reached. In this embodiment the threshold is set in step (430) as the predetermined percentage. The result of the LBR is compared to this predetermine percentage. An example LBR equation is as follows:

$$LBR = \left(1 - \frac{Battery\ Delta_{min}}{Battery\ Delta_{Avg}}\right)$$

In this embodiment, once an LBR is reached that is at or above the select percentage, the threshold has been reached. If it is determined that the threshold has not been reached at (434), the process continues at (432). When a delta voltage average is determined to be at or above the threshold (434) in this embodiment, the process continues by measuring and determining the delta voltage at the next set time to collect the data (436). If a select number of delta voltage collections have not occurred (438), the process continues at (436). This provides another layer of filtering. For example, in one embodiment, a consecutive three day detection of a delta voltage at or above the threshold is required. Once, a select number of delta voltages have been detected at or above the threshold (438), an RRT signal is generated and sent. For example, with the IMD 200 example, the controller 202 will direct a transmitter in the telemetry module 208 to send a signal to the IMD provider. In another embodiment, the controller 202 is configured to store each delta voltage average and dynamically determine thresholds as each delta voltage average is determined. Also, the controller 202 can also be configured to store data relating to the determined thresholds in the memory 210.

Although, the above example embodiment only illustrates the determination of one threshold that is used to determine when to send an RRT signal, it is contemplated that more than one threshold can be set. For example, the first threshold could be set to send an RRT that indicates 60 days of effective battery life and a second threshold could be set to send a RRT signal that indicates 30 days of effective battery life etc. In addition, a multitude of thresholds could be set after the minimum delta voltage to set up a gas gauge like configuration. As illustrated in FIG. 5, the minimum delta voltage occurs roughly at the midpoint of the battery's life. Hence, knowing the approximate midpoint of the life of the battery and with the use of a plurality of thresholds, a gross gas gauge configuration could be implemented. Moreover, although the above example illustrates taking the unloaded voltage before the pulse, in another embodiment, the unloaded voltage is taken after the pulse. Hence, the timing of the measurement of voltages can vary. Moreover, different pulse configurations can be applied.

Figure 7:
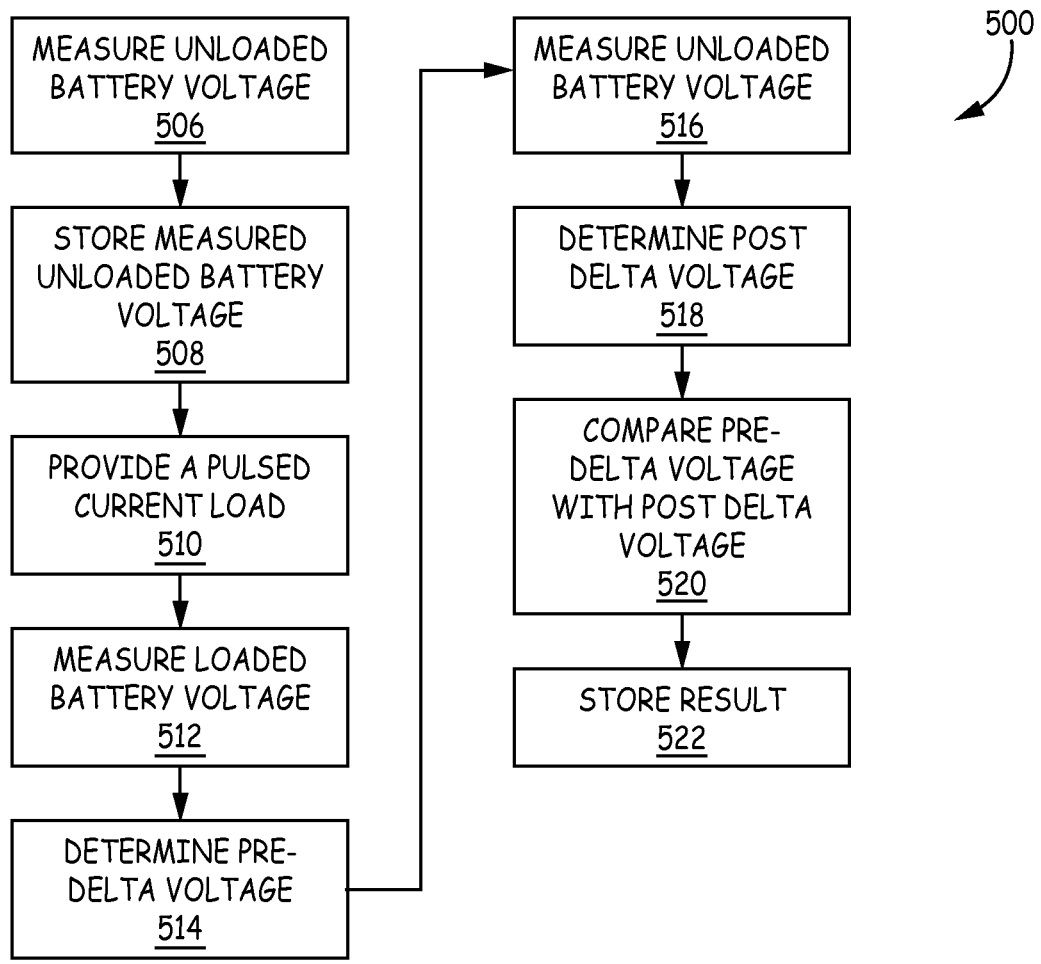
FIG. 7 is a post delta voltage flow diagram of one embodiment of the present invention.

In addition, the use of delta voltages could be used to gather data relating to battery recovery to determine how the battery is handling the current load. For example, like the embodiment in FIG. 6, the delta voltage between the unloaded and the loaded battery can be determined. The voltage on the battery right after the current load pulse can then measured and a post delta voltage between the post pulse unloaded battery voltage and the loaded battery can be determined and compared to an associated pre-delta voltage. Referring to FIG. 7, an example of this embodiment is illustrated on the post delta voltage flow diagram 500. As illustrated, the process starts by measuring the voltage of the battery when it is unloaded (506). The measurement is then stored in memory 210 (508). The process continues by providing a pulsed current load (510). While the current load is being applied, the battery voltage is measured (512). A pre delta voltage, which is the difference between the stored unloaded voltage and the load voltage, is then determined (514). The pre-delta voltage is stored in memory 210. Right after the pulse, the unloaded battery voltage is measured (516). A post delta voltage is then determined (518). The post delta voltage is the difference between the post unloaded battery voltage and the loaded battery voltage. The pre delta voltage is then compared with the post delta voltage (520). The result is then stored in the memory (522). This data can be tracked to determine how the battery is performing throughout its life. If a problem is detected a signal can be generated. Moreover, different pulsing configurations can be used. For example, a plurality of pulses can be applied with voltage monitoring taking place at select times during and after the pulses. Data regarding the battery, including RRT, can be periodically uploaded. For example, in the IMD example provided above, the controller 202 can be configured to implement the telemetry module 208 notify the patient or physician of the status of the battery. Also in embodiments, the controller can be configured to modify the operation of the IMD based on the status of the battery.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:

1. A method of generating at least one recommended replacement time signal for a lithium carbon monofluoride battery in a battery recommended replacement time system for an implantable medical device, said system including a battery monitor, a signal generator, a memory and a controller in communication with the battery monitor, the signal generator and the memory, the method comprising:

first, with the controller monitoring time, waiting more than six months after implantation of the lithium carbon monofluoride battery before determining delta voltage data;

measuring a plurality of associated unloaded and loaded battery voltages with a battery monitor and storing each of the plurality of associated loaded and unloaded battery voltages in the memory;

determining a delta voltage for each associated unloaded and loaded battery voltages by determining the difference between each of the associated unloaded and loaded battery voltages;

averaging sixteen of the determined delta voltages to determine an average delta voltage;

determining, with the controller executing instructions stored in the memory, a minimum delta voltage from a plurality of averaged delta voltages;

determining a plurality of threshold points after the minimum delta voltage is determined; and the controller activating the signal generator to generate a recommended replacement time signal for the lithium carbon monofluoride battery with the use of the minimum delta voltage when at least one averaged delta voltage is detected by the battery monitor that has reached each of the plurality of the threshold points, each of the plurality of threshold points indicating a time of effective battery life remaining, the method of generating at least one recommended replacement time signal for a lithium carbon monofluoride battery being within the implantable medical device.

2. The method of claim 1, further comprising:
selectively coupling a current load to the battery when measuring the battery loaded voltages.

3. The method of claim 1, further comprising:
delaying the generation of the at least one recommended replacement time signal until a select number of consecutive delta voltages have at least reached the replacement threshold.

4. The method of claim 1, further comprising:
measuring a post battery unloaded voltage for each associated unloaded and loaded battery voltages;
determining a post delta voltage from the post battery unloaded voltage and the associated loaded battery voltage; and
comparing the post delta voltage with the delta voltage of the associated unloaded and loaded battery voltages.

5. The method of claim 1 wherein the average delta voltage is a moving average of sixteen delta voltages.

6. The method of claim 1 wherein each of the plurality of associated loaded and unloaded battery voltages is measured once per day for sixteen days.

7. The method of claim 1, further comprising:
indicating the time of effective battery life remaining in the form of a fuel gauge.

8. The method of claim 1, further comprising:
monitoring trends in the plurality of averaged delta voltage data.

9. The method of claim 8, further comprising:
when a rising trend is monitored, determining the minimum delta voltage.

10. The method of claim 8, further comprising:
generating at least one signal based on a monitored trend.

11. A battery recommended replacement time system for an implantable medical device comprising:
a battery monitor coupled to measure a voltage of a lithium carbon monofluoride battery;
a circuit selectively coupled to the lithium carbon monofluoride battery to provide a current load to said battery;
a signal generator configured to generate at least a recommended replacement time threshold signal;
a memory to store instructions and data, the memory including instructions to determine a minimum delta voltage from a plurality of averaged delta voltages, each of the plurality of averaged delta voltages determined from sixteen collected delta voltage data points, wherein each delta voltage is determined by calculating the difference between unloaded and loaded battery voltages; and
a controller in communication with the memory, the battery monitor and the signal generator, the controller configured to selectively couple the circuit to the battery, the controller configured to execute the instruction to determine the minimum delta voltage from the plurality of averaged delta voltages and determine a plurality of threshold points after the minimum delta voltage is determined, the controller still further configured to implement the instructions and process data relating to the determined minimum delta voltage to activate the signal generator when a delta voltage is detected by the battery monitor that has reached each of the threshold points, and the controller further configured to first wait a select period of time more than six months after implantation of the lithium carbon monofluoride battery before gathering delta voltage data and delay activation of the signal generator until a select number of consecutive delta voltages over each of the plurality of threshold points are observed by the battery monitor, the battery recommended replacement time system within the implantable medical device, the plurality of threshold points indicating a time of effective battery life remaining.

12. The battery recommended replacement time system of claim 11, wherein the controller is further configured to monitor trends in the averaged delta voltage data.

13. The battery recommended replacement time system of claim 11, wherein the average delta voltage is a moving average of sixteen delta voltages.

14. The battery recommended replacement time system of claim 11, wherein each of the plurality of associated loaded and unloaded battery voltages is measured once per day for sixteen days.

15. The battery recommended replacement time system of claim 11, wherein the time of effective battery life remaining is in the form of a fuel gauge.

* * * * *